(12) United States Patent
Ben-Sasson et al.

(10) Patent No.: US 9,447,040 B2
(45) Date of Patent: Sep. 20, 2016

(54) TRICYCLIC COMPOUNDS, COMPOSITIONS COMPRISING THEM AND USES THEREOF

(71) Applicant: YISSUM RESEARCH DEVELOPMENT COMPANY OF THE HEBREW UNIVERSITY OF JERUSALEM LTD., Jerusalem (IL)

(72) Inventors: Shmuel Ben-Sasson, Jerusalem (IL); Arie Dagan, Jerusalem (IL); Sharon Perles, Jerusalem (IL)

(73) Assignee: YISSUM RESEARCH DEVELOPMENT COMPANY OF THE HEBREW UNIVERSITY OF JERUSALEM LTD., Jerusalem (IL)

(*) Notice: Subject to any disclaimer, the term of this patent is extended or adjusted under 35 U.S.C. 154(b) by 0 days.

(21) Appl. No.: 14/358,431

(22) PCT Filed: Nov. 15, 2012

(86) PCT No.: PCT/IL2012/050461
§ 371 (c)(1),
(2) Date: May 15, 2014

(87) PCT Pub. No.: WO2013/072915
PCT Pub. Date: May 23, 2013

(65) Prior Publication Data
US 2014/0329877 A1 Nov. 6, 2014

Related U.S. Application Data

(60) Provisional application No. 61/559,964, filed on Nov. 15, 2011, provisional application No. 61/603,508, filed on Feb. 27, 2012.

(51) Int. Cl.
*C07D 209/82* (2006.01)
*C07D 209/88* (2006.01)
*C07D 209/86* (2006.01)

(52) U.S. Cl.
CPC ........... *C07D 209/88* (2013.01); *C07D 209/86* (2013.01)

(58) Field of Classification Search
USPC ......................................... 548/446; 514/411
See application file for complete search history.

(56) References Cited

U.S. PATENT DOCUMENTS

| | | | | |
|---|---|---|---|---|
| 2,590,125 A * | 3/1952 | Robinson | ............. | C07D 279/18 544/41 |
| 2,676,966 A * | 4/1954 | Cusic et al. | ................. | 546/104 |
| 2,930,798 A * | 3/1960 | Schmitt | ........................ | 548/505 |
| 3,836,587 A * | 9/1974 | Grayson | ................. | C08K 5/50 524/115 |
| 6,440,961 B1 | 8/2002 | Lohray et al. | | |
| 6,933,313 B2 | 8/2005 | Harper et al. | | |
| 8,053,436 B1 | 11/2011 | Halazy et al. | | |
| 8,362,277 B2 * | 1/2013 | McKnight | ............. | A61K 31/404 548/444 |
| 8,604,074 B2 * | 12/2013 | McKnight | ............... | A61K 31/00 514/411 |
| 9,095,572 B2 * | 8/2015 | McKnight | ............. | C07D 405/12 |
| 2009/0317372 A1 | 12/2009 | Kiss | | |
| 2011/0015217 A1 * | 1/2011 | McKnight | .............. | A61K 31/00 514/275 |
| 2012/0022096 A1 * | 1/2012 | McKnight | ............. | C07D 405/12 514/292 |

FOREIGN PATENT DOCUMENTS

| | | |
|---|---|---|
| FR | 1186832 A | 9/1959 |
| GB | 832568 A | 4/1960 |
| WO | 9634863 A1 | 11/1996 |
| WO | 0129028 A1 | 4/2001 |
| WO | 0132176 A1 | 5/2001 |
| WO | 03027084 A1 | 4/2003 |
| WO | 2007079239 A2 | 7/2004 |
| WO | 2010081115 A1 | 7/2010 |

OTHER PUBLICATIONS

Chigwada et al. Thermochimica Acta (2005), 436(1-2), pp. 113-121.*
Kawanishi et al. Journal of Physical Chemistry (1986) 90(11), 2469-2475.*
Winbury et al. Journal of Pharmacology and Experimental Therapeutics (1954), 111, 395-403.*
Stephen R. Farmer "Molecular determinants of brown adipocyte formation and function" Gene & Development 22, 1269-1275(May 2008).
Natasa Petrovic et al "Chronic Peroxisome Proliferator-activated Receptor Y (PPARY) Activation of Epididymally Derived White Adipocyte Cultures Reveals a Population of Thermogenically competent, UCP1-containing Adipocytes Molecularly Distinct from Classic Brown Adipocytes" The Journal of Biological Chemistry 258(10) : 7153-7164 (Mar. 2010).
Huruya Ohno et al, "PPAR agonists induce a white-to-brown fat conversion through stavilization of PRDM16 protein" Cell Metabolism 15: 395-404 (Mar. 2012).
Stephen M. Berge et al., "Pharmaceutical Salts' Journal of Pharmaceutical Sciences" 66 : 1-19 (Jan. 1977).
Yuji Kawanishi et al "Unexpected salt effects on Charge Separation Yields in Phenothiazine Derivatives-Methylvlologen Systems" J. Phys. Chem 90: 6034-6037 (Jan. 1986).
Jonathan P Saxe "Your brain on drugs" Nature American. 6 : 639-640 (Sep. 2010).
European Search Report, dated Jun. 26, 2015, in corresponding application No. EP12 850 186.3.

* cited by examiner

*Primary Examiner* — Nyeemah A Grazier
(74) *Attorney, Agent, or Firm* — Browdy and Neimark, PLLC (57) ABSTRACT

Tricyclic compounds, compositions and uses thereof in the treatment of at least one disease, disorder or condition such as for example obesity, overweight, abnormal fat-distribution and any conditions or disease associated therewith.

20 Claims, 4 Drawing Sheets

TRICYCLIC COMPOUNDS, COMPOSITIONS COMPRISING THEM AND USES THEREOF

FIELD OF THE INVENTION

This invention relates to tricyclic compounds, compositions comprising them and uses thereof in the treatment of obesity and related disorders.

BACKGROUND OF THE INVENTION

Obesity is a leading preventable cause of death worldwide, with increasing prevalence in adults and children, considered as one of the most serious and widespread public health problem of the 21$^{st}$ century.

Excessive body weight is associated with various physical and mental diseases and conditions, particularly cardiovascular diseases, diabetes mellitus type 2, obstructive sleep apnea, certain types of cancer, osteoarthritis and depression. As a result, obesity has been found to reduce life expectancy. Once considered a problem only of high-income countries, obesity rates are rising worldwide and affecting both the developed and developing world.

To date, there is an ongoing search for an effective and safe treatment for obesity, abnormal fat-distribution and all health threatening conditions associated therefrom.

Fat tissue or adipose tissue is the loose connective tissue composed of adipocytes. Adipose tissue is derived from lipoblasts. Its main role is to store energy in the form of lipids, although it also cushions and insulates the body. Adipose tissue includes all fat tissue in the body including abdominal fat, epicardial fat and subcutaneous fat.

Adipose tissue has been recognized to participate in endocrine processes, including the production of hormones such as leptin, estrogen, resistin, and cytokine TNFα. Moreover, adipose tissue can affect other organ systems of the body and may lead to disease.

Obesity in humans and most animals does not depend on body weight, but on the amount of adipose tissue.

There are two types of adipose tissue: white adipose tissue (WAT), which primarily stores fat, and brown adipose tissue (BAT), which functions in the process of fat burning for heat production (Farmer S R, *Gene & Development* 22, 1269-1275 (2008), Petrovic N, *JBC* 258, 7153-7164 (2010)). The feasibility of WAT to BAT conversion was demonstrated, for example, by application of PPARγ agonists (Ohno H. et al., *Cell Metabolism* 15: 395-404 (2012)). However, from the whole organism point of view, PPARγ activation has also other effects on other tissues with the end result of increase in body weight in PPARγ agonists treated patients.

One optional strategy for treating obesity and related conditions, diseases and disorders associated with abnormal WAT distribution is to induce the conversion of WAT to BAT. Previous treatment of obesity in such mechanism of action included the use of thiazolidazine compounds which increased the body's sensitivity to insulin. Such compounds showed many adverse effects, including liver toxicity, bone loss, and weight gain.

SUMMARY OF THE INVENTION

The present invention provides a compound of the general formula (I):

wherein
each of $R_1$-$R_8$ is independently selected from the group consisting of H, OH, SH, halogen, nitro, amino, nitrilo, nitroso, acetyl, acetamido, acylamido, alkylamino, straight or branched $C_1$-$C_5$ alkyl, straight or branched $C_1$-$C_5$ alkenyl, straight or branched $C_1$-$C_5$ alkynyl, straight or branched $C_1$-$C_5$ alkoxy, straight or branched $C_1$-$C_5$ carboxyl, straight or branched $C_1$-$C_5$ ester, straight or branched $C_1$-$C_5$ thioxy, straight or branched $C_1$-$C_5$ sulfinyl and straight or branched $C_1$-$C_5$ thionyl;

$R_9$ and $R_{10}$ is independently selected from null, straight or branched $C_1$-$C_9$ alkyl, straight or branched $C_1$-$C_9$ alkenyl, straight or branched $C_1$-$C_9$ alkynyl, piperazinyl, pyridinyl, piperidinyl, morpholinyl and thiomorpholinyl;

wherein each of said $R_9$ and $R_{10}$ are independently optionally substituted with at least one substituent selected from the group consisting of amino (including quarternary ammonium), phosphonium, straight or branched $C_1$-$C_5$ alkoxy, straight or branched $C_1$-$C_5$ carboxyl, straight or branched $C_1$-$C_5$ ester, straight or branched $C_1$-$C_5$ thioxy, straight or branched $C_1$-$C_5$ sulfinyl, straight or branched $C_1$-$C_5$ thionyl;

X is selected from CH, N and P;
Y is selected from null, CH, N, P, —$CH_2$, —NH, O, S, —CH—$CH_2$, —CH=$CH_2$, —C=O and N—C=O.

In a further aspect the invention provides a compound of the general formula (I):

wherein
each of $R_1$-$R_8$ is independently selected from the group consisting of H, OH, SH, halogen, nitro, amino, nitrilo, nitroso, acetyl, acetamido, acylamido, alkylamino, straight or branched $C_1$-$C_5$ alkyl, straight or branched $C_1$-$C_5$ alkenyl, straight or branched $C_1$-$C_5$ alkynyl, amine, straight or branched $C_1$-$C_5$ alkoxy, straight or branched $C_1$-$C_5$ carboxyl, straight or branched $C_1$-$C_5$ ester, straight or branched $C_1$-$C_5$ thioxy, straight or branched $C_1$-$C_5$ sulfinyl, straight or branched $C_1$-$C_5$ thionyl;

$R_9$ and $R_{10}$ is independently selected from null, straight or branched $C_1$-$C_9$ alkyl, straight or branched $C_1$-$C_9$ alkenyl, straight or branched $C_1$-$C_9$ alkynyl, piperazinyl, pyridinyl, piperidinyl, morpholinyl and thiomorpholinyl;

wherein at least one of said $R_9$ and $R_{10}$ is substituted with at least one quaternary amino (ammonium) group or a phosphonium group;

X is selected from CH, N and P;

Y is selected from null, CH, N, P, $CH_2$, NH, O, S, CH—$CH_2$, CH=$CH_2$, C=O and N—C=O.

In some embodiments, Y is null. Under these embodiments the central ring in the tricyclic ring system is a five-membered ring. Thus, under these embodiments, a compound of the invention has a general formula (II):

(II)

In other embodiments, X is N. Under these embodiments a compound of the invention has a general formula (III):

(III)

In further embodiments, X is N and Y is null. Under these embodiments a compound of the invention has a general formula (IV):

(IV)

In further embodiments, $R_9$ is a straight or branched $C_1$-$C_9$ alkyl. In other embodiments, said straight or branched $C_1$-$C_9$ alkyl is substituted with at least one amino. In further embodiments, $R_9$ is a straight or branched $C_1$-$C_9$ alkyl. In other embodiments, said straight or branched $C_1$-$C_9$ alkyl is substituted with at least one quaternary amino group.

In other embodiments, said amino (ammonium) has a general formula (V):

(V)

wherein each of R', R" and R'" is independently selected from a group consisting of straight or branched $C_1$-$C_9$ alkyl, straight or branched $C_1$-$C_9$ alkenyl, straight or branched $C_1$-$C_9$ alkynyl. In some embodiments, each of R', R" and R'" is independently a straight or branched $C_1$-$C_9$ alkyl.

In further embodiments, $R_9$ is a straight or branched $C_1$-$C_9$ alkyl. In other embodiments, said straight or branched $C_1$-$C_9$ alkyl is substituted with at least one phosphonium group. In other embodiments, said phosphonium group has a general formula (VI):

(VI)

wherein each of R', R" and R'" is independently selected from a group consisting of straight or branched $C_1$-$C_9$ alkyl, straight or branched $C_1$-$C_9$ alkenyl, straight or branched $C_1$-$C_9$ alkynyl. In some embodiments, each of R', R" and R'" is independently a straight or branched $C_1$-$C_9$ alkyl.

In other embodiments, at least one of $R_1$-$R_4$ is a halogen. In further embodiments, at least one of $R_5$-$R_8$ is a halogen. In yet other embodiments, at least one of $R_1$-$R_4$ is a halogen and at least one of $R_5$-$R_8$ is a halogen. In some embodiments said halogen is Br.

In other embodiments, at least one of $R_1$-$R_4$ is OH. In further embodiments, at least one of $R_5$-$R_8$ is OH.

In other embodiments, at least one of $R_1$-$R_4$ is a nitro. In further embodiments, at least one of $R_1$-$R_4$ is a nitro and at least one of $R_5$-$R_8$ is a nitro.

The invention also provides a compound selected from the following:

5-(3,6-dibromo-9H-carbazol-9-yl-N,N,N-trimethylpentan-1-aminium (MTK-012)

3-(3,6-dibromo-9H-carbazol-9-yl)-N,N,N-trimethylpropan-1-aminium (MTK-013)

-continued 5-(9H-carbazol-9-yl)-N,N,N-trimethylpentan-1-aminium 5-(2-hydroxy-9H-carbazol-9-yl)-N,N,N-trimethylpentan-1-aminium The term "halogen" is meant to encompass any halogen moiety selected from F, Cl, Br and I.

The term "nitro" is a —NO$_2$ moiety.

The term "amino" refers to —NH$_2$, —NHR, —NRR', wherein R, R' and R" are each independently selected from straight or branched C$_1$-C$_{10}$ alkyl (also termed "alkylamino"), straight or branched C$_2$-C$_{10}$ alkenyl, straight or branched C$_2$-C$_{10}$ alkynyl. The term amino also includes quaternary ammonium moiety of the form —$^+$NRR'R" wherein R, R' and R" are as defined herein above.

The term "nitrilo" refers to —CN,

The term "nitroso" refers to a NO moiety, including C-nitroso moieties (e.g., nitrosoalkanes —R—N=O, wherein R is selected from straight or branched C$_1$-C$_{10}$ alkanyl, straight or branched C$_2$-C$_{10}$ alkenylene, straight or branched C$_2$-C$_{10}$ alkynylene), S-nitroso moieties (nitrosothiols; —S—N=O or —RS—N=O wherein R is selected from straight or branched C$_1$-C$_{10}$ alkanyl, straight or branched C$_2$-C$_{10}$ alkenylene, straight or branched C$_2$-C$_{10}$ alkynylene), N-nitro so moieties (e.g., nitrosamines; —N=N=O, RN—N=O, —RR'N—N=O), and O-nitroso moieties (—O—N=O, —RO—N=O wherein R is selected from straight or branched C$_1$-C$_{10}$ alkanyl, straight or branched C$_2$-C$_{10}$ alkenylene, straight or branched C$_2$-C$_{10}$ alkynylene).

The term "acetyl" refers to a —C(=O)CH$_3$ moiety.

The terms "acetamido" and "acylamido" refers to —CH$_2$C(=O)NH$_2$ and CH$_3$C(=O)NH— respectively.

The term "straight or branched C$_1$-C$_5$ alkyl" and "straight or branched C$_1$-C$_9$ alkyl" encompasses a saturated hydrocarbon chain having between 1 to 5 or 1 to 9 carbon atoms.

The term "straight or branched C$_2$-C$_5$ alkenyl" and "straight or branched C$_2$-C$_9$ alkenyl" encompasses a hydrocarbon chain having between 1 to 5 or 1 to 9 carbon atoms and at least one double bond.

The term "straight or branched C$_2$-C$_5$ alkynyl" and "straight or branched C$_2$-C$_9$ alkynyl" encompasses a hydrocarbon chain having between 1 to 5 or 1 to 9 carbon atoms and at least one triple bond.

The term "straight or branched C$_1$-C$_5$ alkoxy" is meant to encompass an —OR moiety wherein R is selected from a straight or branched C$_1$-C$_{10}$ alkyl, straight or branched C$_2$-C$_{10}$ alkenyl and straight or branched C$_2$-C$_{10}$ alkynyl.

The term "straight or branched C$_1$-C$_5$ carboxyl" refers to a —R—C(=O)OH moiety wherein R is selected from a straight or branched C$_1$-C$_{10}$ alkanyl, straight or branched C$_2$-C$_{10}$ alkenylene and straight or branched C$_2$-C$_{10}$ alkynylene.

The term "straight or branched C$_1$-C$_5$ ester" refers to a RC(=O)O— moiety wherein R is selected from a straight or branched C$_1$-C$_{10}$ alkyl, straight or branched C$_2$-C$_{10}$ alkenyl and straight or branched C$_2$-C$_{10}$ alkynyl.

The term "straight or branched C$_1$-C$_5$ thioxy" refers to a RS— moiety wherein R is selected from a straight or branched C$_1$-C$_{10}$ alkyl, straight or branched C$_2$-C$_{10}$ alkenyl and straight or branched C$_2$-C$_{10}$ alkynyl.

The term "straight or branched C$_1$-C$_5$ sulfinyl" and "straight or branched C$_1$-C$_5$ thionyl" refers to a RS(=O)— moiety wherein R is selected from a straight or branched C$_1$-C$_{10}$ alkyl, straight or branched C$_2$-C$_{10}$ alkenyl and straight or branched C$_2$-C$_{10}$ alkynyl.

The term "phosphonium" refers to a —P$^+$RR'R" moiety wherein R, R' and R" are each selected from a straight or branched C$_1$-C$_{10}$ alkyl, straight or branched C$_2$-C$_{10}$ alkenyl and straight or branched C$_2$-C$_{10}$ alkynyl.

The term "piperazinyl" encompasses a moiety selected from:

The term "pyridinyl" encompasses a moiety:

The term "piperidinyl" encompasses a moiety selected from:

The term "morpholinyl" encompasses a moiety selected from:

The term "thiomorpholinyl" encompasses a moiety selected from:

The compounds of the present invention, as defined above, may have the ability to crystallize in more than one form, a characteristic, which is known as polymorphism, and it is understood that such polymorphic forms ("polymorphs") are within the scope of formulae (I). Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers or as two or more diastereomers. Accordingly, the compounds of this invention include mixtures of enantiomers as well as purified enantiomers or enantiomerically enriched mixtures. Furthermore, the compounds of this invention include mixtures of diastereomers, as well as purified stereoisomers or diastereomerically enriched mixtures. Also included within the scope of the invention are the individual isomers of the compounds of the invention, as defined above, as well as any wholly or partially mixtures thereof. The present invention also covers the individual isomers of the compounds represented by the formulas above as mixtures with isomers thereof in which one or more chiral centers are inverted.

It is also noted that the compounds of the present invention may form tautomers. It is understood that all tautomers and mixtures of tautomers of the compounds of the present invention, are included within the scope of the compounds of the present invention.

In a further aspect, the invention provides a composition comprising a compound of general formula (I), as defined herein above, or any salt thereof.

In some embodiments, said composition is a pharmaceutical composition, wherein said salt is a pharmaceutically acceptable salt.

Pharmaceutical compositions of the invention may additionally comprise any other suitable substances such as other therapeutically useful substances, diagnostically useful substances, pharmaceutically acceptable carriers or the like.

In some embodiments a compound or composition of the invention is administered (suitable to be administered) into an adipose tissue of a subject. In some embodiments said compound or composition of the invention is administered directly into an adipose tissue of a subject. In other embodiments said administration is via injection. In other embodiments, said administration is a transdermal administration. Under such embodiments, transdermal admonition can be achieved by any transdermal formulation known in the art and/or via a transdermal delivery device (for example a patch containing a compound or composition of the invention) at a close proximity to the adipose tissue location of said subject (for example the direct skin or mucosal tissue in contact with said adipose tissue).

Pharmaceutical compositions of the invention comprise a compound of the subject invention in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous, intra-adipose tissue and intradermal) administration or administration via an implant. The compositions may be prepared by any method well known in the art of pharmacy. Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules (including softgel capsules), or as a powder or granules, or as a solution or suspension. The active ingredient may also be presented as a bolus, liquid formulation or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

In some embodiments, compositions of the invention include also compositions where the compound of the invention is formulated in a fat emulsion formulation (i.e. formulated in conventional formulation processes to produce an emulation comprising at least one fat component, either from a natural or synthetic source), such as for example Intralipid formulation (in any concentration).

The exact dose and regimen of administration of the composition will necessarily be dependent upon the therapeutic or nutritional effect to be achieved and may vary with the particular formula, the route of administration, and the age and condition of the individual subject to whom the composition is to be administered.

The invention also includes any salt of a compound of the invention, including any pharmaceutically acceptable salt, wherein a compound of the invention has a net charge (either positive or negative) and at least one counter ion (having a counter negative or positive charge) is added thereto to form said salt. The phrase "pharmaceutically acceptable salt(s)", as used herein, means those salts of compounds of the invention that are safe and effective for pharmaceutical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, iso nicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Salts of the invention may also include a counter anion being a halogen anion such as for example chloride and bromide anions. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 *J. PHARM. SCI.* 1-19 (1977), incorporated herein by reference.

In another aspect the invention provides a compound of general formula (I), as defined herein above, for use as a medicament.

In a further aspect the invention provides a use of a compound of general formula (I), as defined herein above, for the preparation of a medicament.

In some embodiments, said medicament is for the treatment of obesity, and conditions or disease associated therewith.

The term "obesity" is meant to encompass is a condition in a subject having excess body fat. It is defined by body mass index (BMI) and further evaluated in terms of fat distribution via the waist-hip ratio and total cardiovascular risk factors. Additional parameters measuring extent of obesity are percentage body fat and total body fat. Subjects suffering from obesity have a BMI value of above 25. In some embodiments the term "obesity" includes subjects having BMI values of between about 25.0 to about 29.9 (overweight), in some further embodiments between about 30.0 to about 34.9 (class I obesity), in yet further embodiments between about 35.0 to about 39.9 (class II obesity), in further embodiments above 40.0 (class III obesity), in other embodiments between about 40 to about 49.9 (morbid obesity) and in other embodiments ≥50 (super obesity).

In other embodiments, said medicament is for the treatment of abnormal fat-distribution and conditions or disease associated therewith.

The term "abnormal fat-distribution" is meant to encompass any irregular fat tissue distribution in, near or on an organ of a subject or parts thereof. Fat or adipose tissue includes all fat tissue in the body including abdominal fat, epicardial fat and subcutaneous fat. The term is further meant to encompass any irregular fat tissue distribution as perceived by the affected person and thereby is associated with poor self-image and psychiatric disorders related to it.

In some embodiments, conditions or disease associated with obesity, or abnormal fat-distribution include, but are not limited to: diabetes, cardiovascular diseases, obstructive sleep apnea, lipoma, cancer, osteoarthritis, endocrinologic disease and disorders, reproductive disease and disorders, neurological diseases and disorders, psychiatric diseases and disorders, rheumatological diseases and disorders and orthopedic disease and disorders and any combinations thereof.

The invention further provides a use of a compound of general formula (I), as defined herein above, for the preparation of a composition for the remodeling of white adipose tissue (WAT) to brown-like adipose tissue (BAT).

WAT adipocytes, contain a single lipid droplet. BAT adipocytes contain numerous smaller lipid droplets and a higher number of mitochondria. BAT also contains more blood-capillaries than WAT.

The term "remodeling of white adipose tissue (WAT) to brown-like adipose tissue (BAT)" is meant to encompass any qualitative or quantitative difference or change in the histology of WAT between the initial WAT condition and the WAT condition after treatment. Said qualitative or quantitative difference may be manifested by a change in WAT adipocytes size, ablation thereof, including macrophage-associated liponecrosis, and in appearance of BAT-like adipocytes.

The invention further provides a use of a compound of general formula (I), as defined herein above, for the preparation of a composition for the treatment of a disease, disorder or condition associated with or benefiting from the remodeling of WAT to BAT.

The invention also provides a use of a compound of general formula (I), as defined herein above, for the preparation of a composition for reducing the white adipose tissue (WAT) of a subject in need thereof.

It is to be noted that a reduction of WAT may be measured in any way known to a person skilled in the art, such as for example the reduction of tissue thickness, change in tissue density and so forth. Such reduction in WAT in a subject administered with a compound of the invention may be for any known purposes, such as for example cosmetic, medical (i.e. the treatment of conditions and diseases associated with excess or abnormal levels of WAT), or both.

In a further aspect the invention provides a compound of general formula (I), as defined herein above, for use in the treatment of obesity, and conditions or disease associated therewith.

In a further aspect the invention provides a compound of general formula (I), as defined herein above, for use in the treatment of abnormal fat-distribution and conditions or disease associated therewith.

The invention further provides a compound of general formula (I), as defined herein above, for use in the remodeling of white adipose tissue to brown-like adipose tissue.

The invention further provides a compound of general formula (I), as defined herein above, for use in the treatment of a disease, disorder or condition associated with or benefiting from the remodeling of white adipose tissue to brown-like adipose tissue.

The invention also provides a compound of general formula (I), as defined herein above, for use in reducing the white adipose tissue of a subject in need thereof.

The invention further provides a compound as defined hereinabove for use in the inhibition of protein kinase CDC42-binding-protein-kinase-alpha (CDC42BPA or MRCKA).

It is noted that screening of compound of the invention 5-(3,6-dibromo-9H-carbazol-9-yl)-N,N,N-trimethylpentan- 1-aminium (MTK-012) against 191 different protein kinases showed significantly selective inhibition of protein kinase CDC42-binding-protein-kinase-alpha (also known as CDC42BPA or MRCKA).

In some embodiments said inhibition is associated with the treatment of at least one disease, disorder or condition selected from obesity, overweight or abnormal fat-distribution and conditions or disease associated therewith.

In another one of its aspects the invention provides a method of treating obesity, and conditions or disease associated therewith in a subject in need thereof, wherein said method comprises the administration of an effective amount of a compound of general formula (I), as defined herein above.

In another one of its aspects the invention provides a method of treating abnormal fat-distribution and conditions or disease associated therewith in a subject in need thereof, wherein said method comprises the administration of an effective amount of a compound of general formula (I), as defined herein above.

In a further aspect the invention provides a method of activating the remodeling of white adipose tissue to brown-like adipose tissue in a subject, comprising administrating to said subject an effective amount of a compound of general formula (I), as defined herein above.

In a further aspect the invention provides a method of treating a disease, disorder or condition associated with or benefiting from the remodeling of white adipose tissue to brown-like adipose tissue in a subject, comprising administrating to said subject an effective amount of a compound of general formula (I), as defined herein above.

The term "treatment" as used herein refers to the administering of a therapeutic amount of a compound and/or a composition of the present invention which is effective to ameliorate undesired symptoms associated with a disease, to prevent the manifestation of such symptoms before they occur, to slow down the progression of the disease or condition, slow down the deterioration of symptoms, to enhance the onset of remission period, slow down the irreversible damage caused in the progressive chronic stage of the disease or condition, to delay the onset of said progressive stage, to lessen the severity or cure the disease or condition, to improve survival rate or more rapid recovery, or to prevent the disease or condition form occurring or a combination of two or more of the above.

The "effective amount" for purposes disclosed herein is determined by such considerations as may be known in the art. The amount must be effective to achieve the desired therapeutic effect as described above, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the compound to its target protein(s), its distribution profile within the body, a variety of pharmacological parameters such as half life in the body, on undesired side effects, if any, on factors such as body-weight, BMI, age and gender, etc.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any integer or step or group of integers and steps.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Example 1

Preparation of 5-(3,6-dibromo-9H-carbazol-9-yl)-N,N,N-trimethylpentan-1-aminium chloride (MTK-012)

1.00 g (3.0 mM) 3,6-dibromocarbazole was dissolved in 100 ml dimethylformamide (DMF). 0.57 g (3.0 mM). (5-bromopentyl)-trimethyl-ammonium bromide was added at once. After 10 min of magnetic stirring 1.40 g (10 mM) potassium carbonate was added. After additional 10 min of stirring the temperature was raised to 50° C. and the mixture was stirred at this temperature for 4 h. After cooling to RT the solution was transferred to a separatory funnel and 200 ml of $H_2O$ and 200 ml dichloromethane were added. The solvent mixture was shaken and the lower phase was collected. The upper aqueous phase was extracted four times with 50 ml 3:1 dichloromethane:methanol and the 5 lower phases were combined and washed with 100 ml saturated sodium chloride solution. Dried with $MgSO_4$, filtered and evaporated to dryness. The residue was crystallized from $H_2O$. Yield: 1.28 g. Proton NMR in $CD_3OD$: 1.31 m 2H, 1.70 m 2H, 1.93 m 2H, 3.01 s 9H, 3.16 m 2H, 4.39 t 2H, J=0.6, 7.47 d 2H, J=2.0, 7.54 dd 2H, J1=2.0, J2=0.4, 8.21 d 2H, J=0.4. MS: 451, 453, 455 $M^+$ (symmetrical 2Br triplet) 452, 454, 456 $(MH)^+$ (symmetrical 2Br triplet).

Example 2

Preparation of 5-(3,6-dibromo-9H-carbazol-9-yl)-N,N,N-trimethyl-propan-1-aminium chloride 1.2 g (3.7 mM) 3,6-dibromocarbazole were dissolved in 150 ml dimethylformamide (DMF). 1.0 g (3.8 mM). (5-bromopentyl)-trimethyl-ammonium bromide was added at once. After 10 min of magnetic stirring 1.40 g (10 mM) potassium carbonate was added. After additional 10 min of stirring the temperature was raised to 50° C. and the mixture was stirred at this temperature for 4 h. After cooling to RT the solution was transferred to a separatory funnel and 200 ml of sodium hydroxide 0.5 N and 200 ml dichloromethane were added. The solvent mixture was shaken and the lower phase was collected. The upper aqueous phase was extracted four times with 50 ml 3:1 dichloromethane:methanol and the 5 lower phases were combined and washed with 100 ml saturated sodium chloride solution. Dried with $MgSO_4$, filtered and evaporated to dryness. Yield: 1.1 g.

Example 3

Preparation of 5-(9H-carbazol-9-yl)-N,N,N-trimethylpentan-1-aminium chloride 335 mg (2.0 mM) carbazole were dissolved in 50 ml dimethylformamide (DMF). 0.4 g (2.1 mM). (5-bromopentyl)-trimethyl-ammonium bromide was added at once. After 10 min of magnetic stirring 8.4 g (6.0 mM) potassium carbonate was added. After additional 10 min of stirring the temperature was raised to 50° C. and the mixture was stirred at this temperature for 4 h. After cooling to RT the solution was transferred to a separatory funnel and 100 ml of $H_2O$ and 100 ml dichloromethane were added. The solvent mixture was shaken and the lower phase was collected. The upper aqueous phase was extracted four times with 30 ml 3:1 dichloromethane:methanol and the 5 lower phases were combined and washed with 60 ml saturated sodium chloride solution. Dried with $MgSO_4$, filtered and evaporated to dryness. Yield: 0.75 g.

Example 4

Preparation of 5-(2-hydroxy-9H-carbazol-9-yl)-N,N,N-trimethylpentan-1-aminium chloride 458 mg (2.5 mM) 2-hydroxycarbazole were dissolved in 80 ml dimethylformamide (DMF). 0.51 g (2.5 mM). (5-bromopentyl)-trimethyl-ammonium bromide was added at once. After 10 min of magnetic stirring 1.1 g (7.5 mM) potassium carbonate was added. After additional 10 min of stirring the temperature was raised to 50° C. and the mixture was stirred at this temperature for 4 h. After cooling to RT the solution was transferred to a separatory funnel and 100 ml of $H_2O$ and 100 ml dichloromethane were added. The solvent mixture was shaken and the lower phase was collected. The upper aqueous phase was extracted four times with 40 ml 3:1 dichloromethane:methanol and the 5 lower phases were combined and washed with 60 ml saturated sodium chloride solution. Dried with $MgSO_4$, filtered and evaporated to dryness. Yield: 0.6.

Example 5

Preparation of 5-(3,6-dibromo-9H-carbazol-9-yl)-N,N,N-trimethylpentan-1-aminium chloride 1.00 g (3.0 mmole) 3,6-dibromocarbazole was dissolved in 100 ml Acetonitrile ($CH_3CN$). 0.63 g (3.3 mmole). (5-bromopentyl)-trimethyl-ammonium bromide was added at once. After 10 min of magnetic stirring at room temperature (RT), 1.55 g (11 mmole) potassium carbonate (anhydrous) was added. The temperature was raised to 75° C. and the mixture was stirred at this temperature for 5 h. After cooling to RT the solution was transferred to a round bottom flask and evaporated to dryness. Then 200 ml $H_2O$ and 200 ml n-butyl alcohol were added and the solution was transferred to a separatory funnel. The solvents mixture was shaken and the upper butanolic phase was collected. The lower aqueous phase was extracted with 150 ml n-butyl alcohol. The two butanolic phases were combined and then washed one time with 200 ml saturated sodium chloride containing 0.5N HCl and 4 times with 200 ml saturated sodium chloride solution. Water-dried with $MgSO_4$, filtered and evaporated to dryness. The product was crystallized from $H_2O$. Yield: 1.49 g. Proton NMR in $CD_3OD$: 1.31 m 2H, 1.70 m 2H, 1.93 m 2H, 3.01 s 9H, 3.16 m 2H, 4.39 t 2H, J=0.6, 7.47 d 2H, J=2.0, 7.54 dd 2H, J1=2.0, J2=0.4, 8.21 d 2H, J=0.4. MS: 451, 453, 455 $M^+$ (symmetrical 2Br triplet) 452, 454, 456 $(MH)^+$ (symmetrical 2Br triplet).

Example 6

Intraperitoneal (i.p.) Injection of MTK-012 to Mice 42 wks old male mice (35-42 g body wt.) were i.p. injected with either vehicle (=Control, 10 mice) or with MTK-012 dissolved in that vehicle (10 mice).

Vehicle composition: aqueous solution of 4% Tween20 (Sigma, P7949) and 20% Propylene-Glycol (Sigma, P4347).

MTK-012 was dissolved in vehicle composition at a final concentration of 5 mg/ml.

Figure 1:
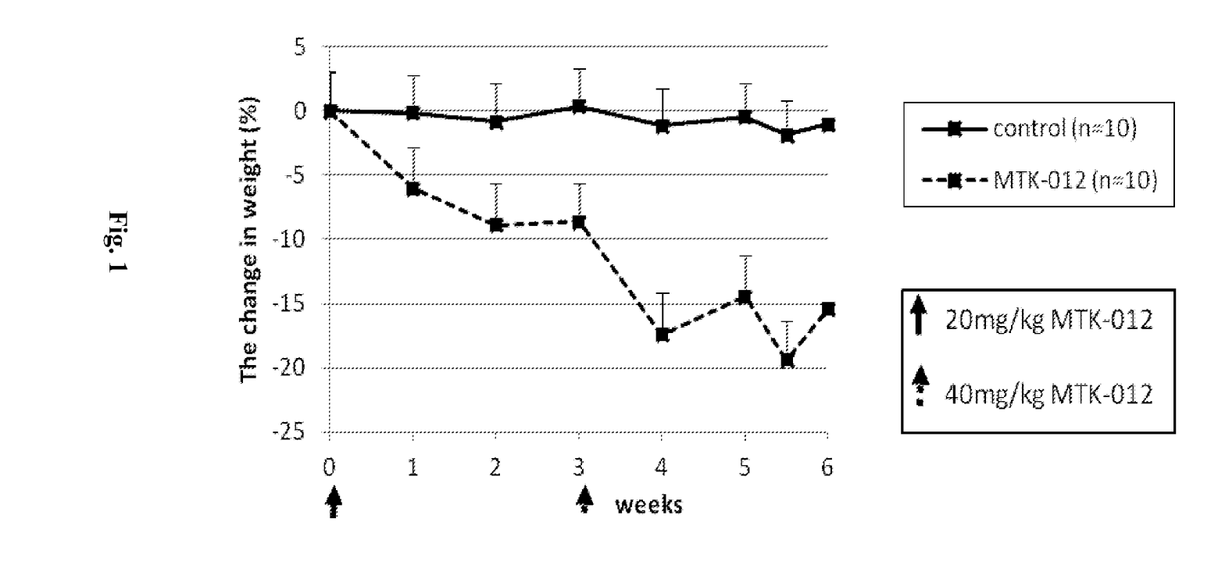
FIG. 1 demonstrates the change in body weight of 42 weeks old male mice following intraperitoneal injection of 5-(3,6-dibromo-9H-carbazol-9-yl)-N,N,N-trimethylpentan-1-aminium (MTK-012).

The mice were initially (t=0) injected a dose of 20 mg/kg, or the equivalent volume of vehicle to the controls (solid arrow in FIG. 1). Three weeks later the mice were injected a double dose of 40 mg/kg of MTK-012 or 40 mg/kg of vehicle (broken arrow in FIG. 1).

Body weight was measured once a week; the results are shown in FIG. 1 and expressed as the % change in body weight relative to the body weight on day 0. The animals in the treated group were well and active, similar to the controls.

Figure 2A:
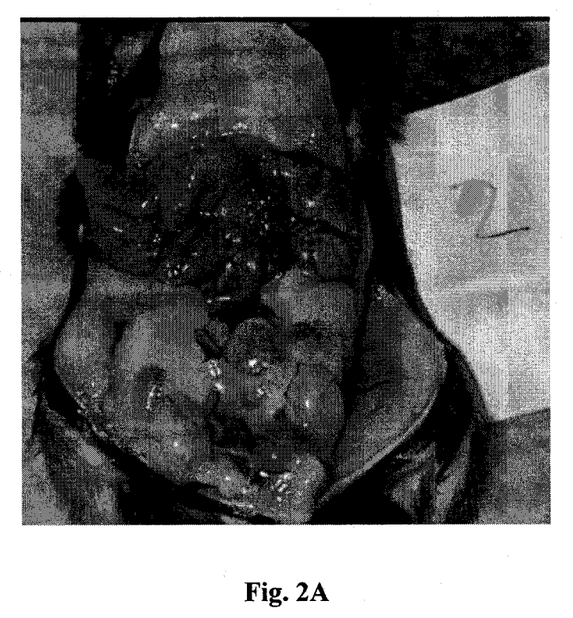
FIGS. 2A-2B provides a representative illustration of the reduction in abdominal fat-mass of the MTK-012 treated mice following the termination of the experiment (control (FIG. 2A) and treated animal (FIG. 2B), as described in Example 5).
Figure 2B:
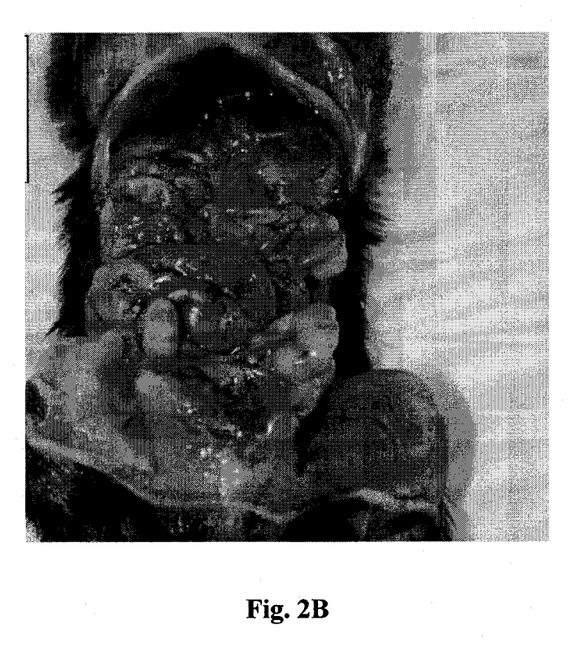

At t=6 wks the animals were sacrificed and dissected for gross pathology. No apparent change was noted except for the ablation of the abdominal adipose tissue in the MTK-012 treated mice, as illustrated in FIGS. 2A-2B, showing an apparent difference in abdominal adipose tissue between the untreated animal (FIG. 2A) and the treated one (FIG. 2B).

Example 7

Single Subcutaneous (s.c.) Injection of MTK-012 Resulted in Substantial Reduction in s.c. Fat SD male rats of about 400 g body weight were s.c. injected once (t=0) following light anesthesia with Ketamine-Xylazine.

MTK-012, at a final concentration of 10 mg/ml, was dissolved in a vehicle containing: 2.3% sodium decanoate (C10, Sigma, C4151), 2.3% sodium dodecanoate (C12, Sigma, L9755), 10% Solutol HS 15 (BASF, cat#06466701), 40% Propylene-Glycol (Sigma, P4347) and 45% Triacetin (Aldrich, cat#525073).

The injection of 1 ml MTK-012 (=25 mg/kg) was performed as follows: the left side of the rats body was shaved and s.c. injections, 0.2 ml each, were administered at 5 sites, equally distributed along the left side of the rats. The rats were sacrificed after 3 weeks and inner part of their skin was examined. It is evident that the s.c. adipose tissue was reduced (visibly shown) in the treated rats (FIGS. 3B and 3D), as manifested by the exposure of the underneath blood vessels, as compared with the same anatomical area in FIGS.

Figure 3A:
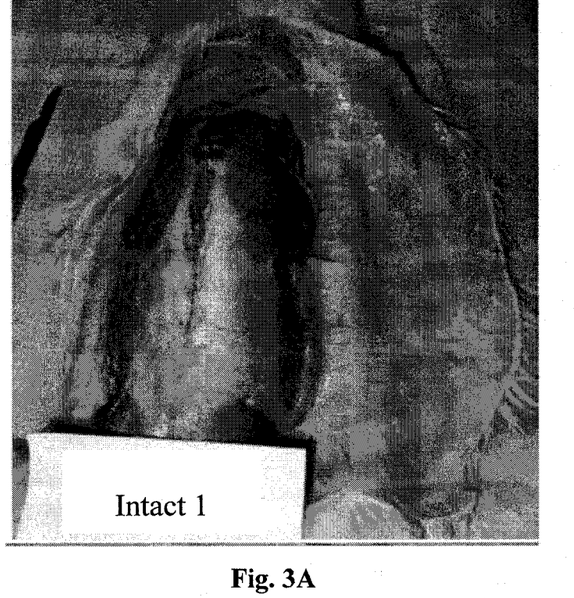
FIGS. 3A-3D provides a representative illustration of the reduction in subcutaneous fat 3 weeks after a single s.c. administration of MTK-012 to rats. The reduction of s.c. fat is manifested by the clear visibility of the underlining blood vessels which are otherwise hindered under a fatty layer in the control rats (Intact—FIGS. 3A and 3C, as compared with treated animals in FIGS. 3B and 3D).
Figure 3B:
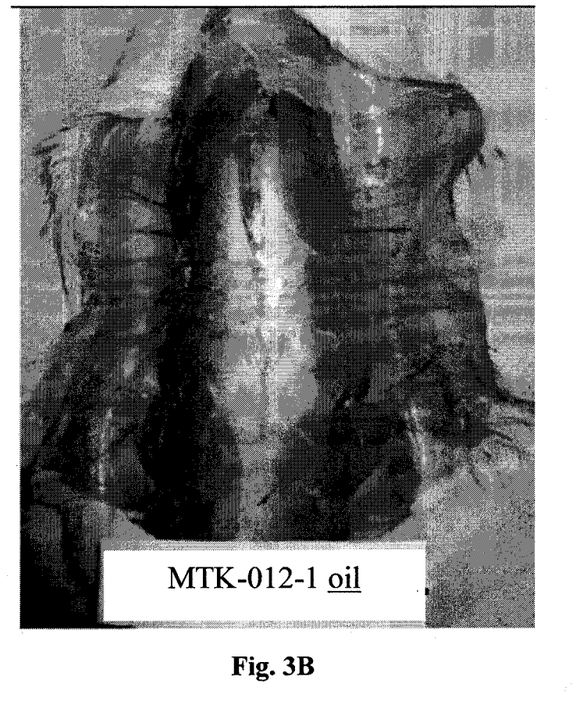
Figure 3C:
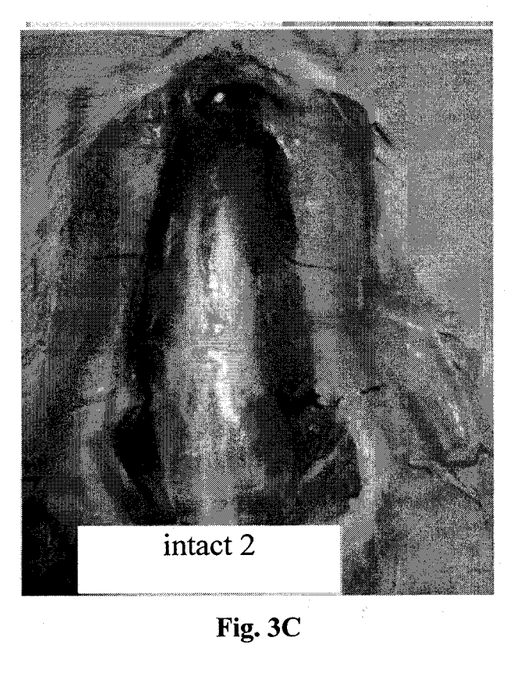
Figure 3D:
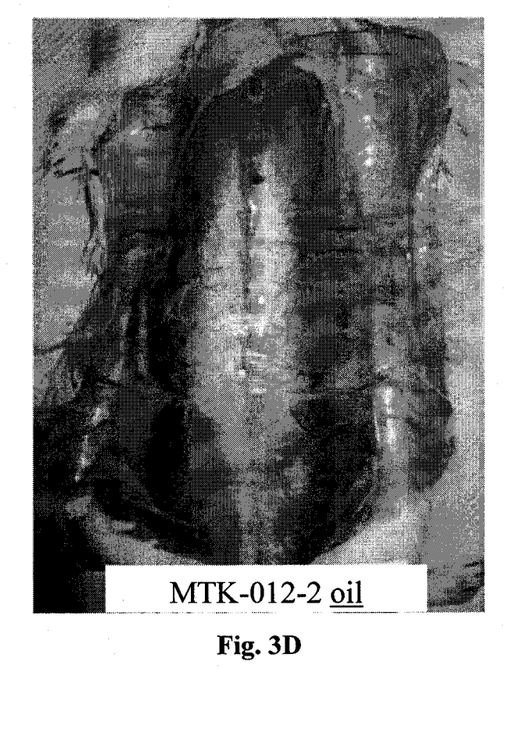

3A and 3C. It should be noted that although the injection was performed unilaterally, the effect expand to the entire subcutis.

Example 8

Intra-Nap Fat-Pad Injection of MTK-012 and MTK-013 to Psammomys

Animals

Ten 2-month old female pasmmomys were subjected to high-fat diet for 5 weeks prior to commencement of experiment.

Treatment Groups

Group I:

0.1 ml vehicle (2.3% sodium decanoate (C10, Sigma, C4151), 2.3% sodium dodecanoate (C12, Sigma, L9755), 10% Solutol HS 15 (BASF, cat#06466701), 40% Propylene-Glycol (Sigma, P4347) and 45% Triacetin (Aldrich, cat#525073))

Group II:

0.1 ml MTK-012 (concentration of 4 mg/ml in above vehicle).

Group III:

0.1 ml MTK-013 (concentration of 4 mg/ml in above vehicle).

Administration

Intra nap fat-pad injections of each composition were administered to animals in each treatment groups (3, 3, and 4 animals in each treatment group respectively), twice a week for 2 weeks, while on high-fat diet. All animals were sacrificed after 4 days from last injection.

Results

Table 1 below provides the results of nap WAT weight after 4 days from treatment. It is clear that significant reduction in WAT was observed when treated with MTK-012 and MTK-013 (treatment groups II and III) as compared with vehicle (treatment group I).

Additionally, extensive fat necrosis without inflammation was observed for treatment groups II and III. Histological examination of WAT tissue showed giant adipocytes in the necrotic site and in the surrounding adipose tissue. Additionally, treated tissue showed smaller than normal adipocytes and increased vascularity in regions away from the site of necrosis, as compared to control group.

TABLE 1

| Nap WAT weight after 4 days from end of treatment | | |
| --- | --- | --- |
| Treatment Group | Nap WAT (g) | Average (g) ± SEM |
| Group I - Vehicle | 5.7 | 5.30 ± 0.21 |
|  | 5.0 |  |
|  | 5.2 |  |
| Group II - MTK-012 | 4.6 | 3.85 ± 0.34 |
|  | 3.0 | (P~0.01)* |
|  | 3.7 |  |
|  | 4.1 |  |
| Group III - MTK-013 | 3.8 | 3.33 ± 0.23 |
|  | 3.1 | (P < 0.01)* |
|  | 3.1 |  |

*by student t-test

The invention claimed is:

1. A compound of the general formula (I):

wherein:
each of $R_1$-$R_8$ is independently selected from the group consisting of H, OH, SH, halogen, nitro, amino, nitrilo, nitroso, acetyl, acetamido, acylamido, alkylamino, straight or branched $C_1$-$C_5$ alkyl, straight or branched $C_1$-$C_5$ alkenyl, straight or branched $C_1$-$C_5$ alkynyl, amine, straight or branched $C_1$-$C_5$ alkoxy, straight or branched $C_1$-$C_5$ carboxyl, straight or branched $C_1$-$C_5$ ester, straight or branched $C_1$-$C_5$ thioxy, straight or branched $C_1$-$C_5$ sulfinyl and straight or branched $C_1$-$C_5$ thionyl;

$R_9$ is selected from the group consisting of straight or branched $C_1$-$C_9$ alkyl, straight or branched $C_1$-$C_9$ alkenyl, straight or branched $C_1$-$C_9$ alkynyl, piperazinyl, pyridinyl, piperidinyl, morpholinyl and thiomorpholinyl each being substituted with at least one quarternary amino group;

at least one of $R_1$-$R_4$ is a halogen or nitro, and at least one of $R_5$-$R_8$ is a halogen or nitro; or at least one of $R_1$-$R_4$ or at least one of $R_5$-$R_8$ is OH;

X is selected from the group consisting of CH, N and P; and

Y is null.

2. A compound according to claim 1, wherein X is N, and Y is null.

3. A compound according to claim 1, wherein $R_9$ is a straight or branched $C_1$-$C_9$ alkyl.

4. A compound according to claim 1, wherein $R_9$ is a straight or branched $C_1$-$C_9$ alkyl substituted by at least one quaternary amino group having a general formula (V):

wherein each of R', R" and R'" is independently selected from the group consisting of straight or branched $C_1$-$C_9$ alkyl, straight or branched $C_1$-$C_9$ alkenyl and straight or branched $C_1$-$C_9$ alkynyl.

5. A compound according to claim 1, wherein at least one of $R_1$-$R_4$ is a halogen.

6. A compound according to claim 1, wherein at least one of $R_5$-$R_8$ is a halogen.

7. A compound according to claim 1, wherein at least one of $R_1$-$R_4$ is a halogen and at least one of $R_5$-$R_8$ is a halogen.

8. A compound according to claim 1, wherein at least one of $R_1$-$R_4$ is OH.

9. A compound according to claim 1, wherein at least one of $R_5$-$R_8$ is OH.

10. A compound according to claim 1, wherein at least one of $R_1$-$R_4$ is a nitro and at least one of $R_5$-$R_8$ is a nitro.

11. A compound according to claim 1, having a general formula (IV):

(IV)

wherein $R_1$-$R_8$ are as defined above; and $R_9$ is a straight or branched $C_1$-$C_9$ alkyl, substituted with a group of the general formula (V):

(V)

wherein each of R', R" and R''' is independently selected from the group consisting of straight or branched $C_1$-$C_9$ alkyl, straight or branched $C_1$-$C_9$ alkenyl and straight or branched $C_1$-$C_9$ alkynyl.

12. A compound according to claim 1, being selected from:
3-(3,6-dibromo-9H-carbazol-9-yl)-N,N,N-trimethylpropan-1-aminium;
5-(9H-carbazol-9-yl)-N,N,N-trimethylpentan-1-aminium;
5-(2-hydroxy-9H-carbazol-9-yl)-N,N,N-trimethylpentan-1-aminium; or
5-(3,6-dibromo-9H-carbazol-9-yl)-N,N,N-trimethylpentan-1-aminium.

13. A composition comprising a compound according to claim 1, or any salt thereof, and a pharmaceutically acceptable vehicle.

14. A composition comprising a compound according to claim 1, or any salt thereof, and a pharmaceutically acceptable vehicle, suitable for administration into an adipose tissue.

15. A composition comprising a compound according to claim 1, or any salt thereof, and a pharmaceutically acceptable vehicle being formulated in a fat emulsion formulation.

16. A method of treating at least one disease, disorder or condition selected from the group consisting of obesity, overweight or abnormal fat-distribution and conditions or disease associated therewith in a subject in need thereof, wherein said method comprises the administration of an effective amount of the compound of claim 1 to the subject.

17. A method according to claim 16, wherein said conditions or disease associated with obesity, overweight or abnormal fat-distribution are selected from the group consisting of diabetes, cardiovascular diseases, obstructive sleep apnea, lipoma, cancer, osteoarthritis, endocrinologic disease and disorders, reproductive disease and disorders, neurological diseases and disorders, psychiatric diseases and disorders, rheumatological diseases and disorders and orthopedic disease and disorders.

18. A method of remodeling of white adipose tissue to brown-like adipose tissue in a subject, comprising administrating to said subject an effective amount of the compound of claim 1.

19. A method according to claim 17, wherein said compound is administered directly into an adipose tissue of said subject.

20. A method according to claim 17, wherein said compound is formulated in a fat emulsion formulation.

* * * * *

UNITED STATES PATENT AND TRADEMARK OFFICE
CERTIFICATE OF CORRECTION

PATENT NO. : 9,447,040 B2
APPLICATION NO. : 14/358431
DATED : September 20, 2016
INVENTOR(S) : Shmuel Ben-Sasson et al.

It is certified that error appears in the above-identified patent and that said Letters Patent is hereby corrected as shown below:

In the Specification

Column 2, Lines 21, 60:
Please replace '$C_1$-$C_5$ alkenyl' at each occurrence with -$C_2$-$C_5$ alkenyl- Column 2, Lines 22, 61:
Please replace '$C_1$-$C_5$ alkynyl' at each occurrence with -$C_2$-$C_5$ alkynyl- Column 2, Lines 28, 67; Column 4, Lines 3, 20:
Please replace '$C_1$-$C_9$ alkenyl' at each occurrence with -$C_2$-$C_9$ alkenyl- Column 2, Line 29; Column 3, Line 1; Column 4, Lines 4, 21:
Please replace '$C_1$-$C_9$ alkynyl' at each occurrence with -$C_2$-$C_9$ alkynyl- Column 5, Line 66; Column 6, Line 3:
Please replace 'between 1 to 5 or 1 to 9 carbon atoms' at each occurrence with -between 2 to 5 or 2 to 9 carbon atoms- In the Claims Column 16, Line 20, Claim 1:
Please replace '$C_1$-$C_5$ alkenyl' with -$C_2$-$C_5$ alkenyl- Column 16, Line 20, Claim 1:
Please replace '$C_1$-$C_5$ alkynyl' with -$C_2$-$C_5$ alkynyl- Column 16, Lines 27-28, Claim 1; Column 16, Lines 56, Claim 4; Column 17, Line 30, Claim 11:
Please replace '$C_1$-$C_9$ alkenyl' at each occurrence with -$C_2$-$C_9$ alkenyl- Signed and Sealed this
First Day of February, 2022

Drew Hirshfeld
*Performing the Functions and Duties of the
Under Secretary of Commerce for Intellectual Property and
Director of the United States Patent and Trademark Office*

Column 16, Line 28, Claim 1; Column 16, Line 57, Claim 4; Column 17, Line 31, Claim 11:
Please replace 'C$_1$-C$_9$ alkynyl' at each occurrence with -C$_2$-C$_9$ alkynyl-